(12) United States Patent
Ross et al.

(10) Patent No.: US 9,919,052 B2
(45) Date of Patent: Mar. 20, 2018

(54) BIORESORBABLE MICROPARTICLES

(75) Inventors: Alistair Ross, East Kilbride (GB); Jennifer S. Law, Glasgow (GB); Fiona E. McInnes, Glasgow (GB)

(73) Assignee: Ferring B.V., Hoofddorp (NL)

( * ) Notice: Subject to any disclaimer, the term of this patent is extended or adjusted under 35 U.S.C. 154(b) by 373 days.

(21) Appl. No.: 14/128,487

(22) PCT Filed: Jun. 20, 2012

(86) PCT No.: PCT/EP2012/061791
§ 371 (c)(1),
(2), (4) Date: Mar. 31, 2014

(87) PCT Pub. No.: WO2012/175538
PCT Pub. Date: Dec. 27, 2012

(65) Prior Publication Data
US 2014/0205665 A1 Jul. 24, 2014

(30) Foreign Application Priority Data
Jun. 23, 2011 (GB) .................................. 1110601.0

(51) Int. Cl.
| | | |
|---|---|---|
| A61L 27/18 | (2006.01) | |
| A61L 27/52 | (2006.01) | |
| C08G 18/40 | (2006.01) | |
| C08G 18/42 | (2006.01) | |
| C08G 18/75 | (2006.01) | |
| A61F 2/06 | (2013.01) | |
| A61L 27/58 | (2006.01) | |
| A61K 47/34 | (2017.01) | |
| A61K 9/16 | (2006.01) | |
| A61K 9/00 | (2006.01) | |
| A61K 9/12 | (2006.01) | |
| A61K 38/21 | (2006.01) | |
| A61K 38/22 | (2006.01) | |
| A61K 38/27 | (2006.01) | |
| C08G 18/38 | (2006.01) | |

(52) U.S. Cl.
CPC ............ *A61K 47/34* (2013.01); *A61K 9/0019* (2013.01); *A61K 9/0051* (2013.01); *A61K 9/12* (2013.01); *A61K 9/1641* (2013.01); *A61K 9/1647* (2013.01); *A61K 38/212* (2013.01); *A61K 38/215* (2013.01); *A61K 38/217* (2013.01); *A61K 38/22* (2013.01); *A61K 38/27* (2013.01); *C08G 18/3831* (2013.01); *C08G 18/4261* (2013.01); *C08G 18/4277* (2013.01); *Y10T 428/2982* (2015.01)

(58) Field of Classification Search
CPC .............. A61K 9/1647; C08G 18/3831; C08G 18/4261; C08G 18/4277; Y10T 428/298
See application file for complete search history.

(56) References Cited

U.S. PATENT DOCUMENTS 6,007,845 A * 12/1999 Domb et al. .................. 424/501

FOREIGN PATENT DOCUMENTS

| | | | |
|---|---|---|---|
| EP | 0016652 | 10/1980 | |
| EP | 0016654 | 10/1980 | |
| EP | 1555278 | * 7/2005 | ........... C08G 63/664 |
| JP | H06-072863 A | 3/1994 | |
| WO | WO 9964491 | 12/1999 | |
| WO | WO 2004/029125 | 4/2004 | |
| WO | WO 2005/068533 | 7/2005 | |
| WO | WO2006/010278 | 2/2006 | |
| WO | WO 2008/047100 | 4/2008 | |

OTHER PUBLICATIONS

De Groot et al., "New biomedical polyurethane ureas with high tear strengths," Poly. Bull., 1997, 38, 211-18.
Rosler et al., "Advanced drug delivery via self-assembly of amphiphillic block copolymers," Adv. Drug Deliv. Rev., 2001, 53(1), 95-108 (Abstract).
Zhu et al., "Synthesis and characterization of poly($\epsilon$-caprolactone)-poly(ethylene glycol) block copolymer," J. Poly. Sci., 1997, 35(4): 709-14 (Abstract).
European Office Action in Application No. 12728095.6, dated Nov. 5, 2015, 4 pp.
Japanese Office Action in Application No. 2014-516321, dated May 31, 2016, 5 pp. (with English translation).

* cited by examiner

Primary Examiner — Anna Falkowitz
(74) Attorney, Agent, or Firm — Fish & Richardson P.C.

(57) ABSTRACT

Polyurethane microparticles are derived from structural units comprising poly(alkylene oxide) moieties, caprolactone moieties and urethane moieties. The microparticles may include an active agent and have a particle size from 0.1 to 100 microns. Microparticles for injection have a particle size of 15 to 80 microns; for use as a aerosol 1 to 3 microns; and for intraocular use 0.02 to 2 microns. Dispersivity is in the range 1 to 3.

29 Claims, 2 Drawing Sheets

Figure 1. Particle size distribution of microparticles prepared in Example 11 as determined by dynamic light scattering.

Figure 2. SEM image of microparticles prepared in Example 17.

BIORESORBABLE MICROPARTICLES

CROSS REFERENCE TO RELATED APPLICATIONS

This is a U.S. National Phase application under 35 U.S.C. § 371 of International Patent Application No. PCT/EP2012/061791, filed Jun. 20, 2012, which published as WO2012/175538, and which claims the priority of Great Britain Patent Application No. 1110601.0 filed on Jun. 23, 2011. The foregoing applications and WO2012/175538 are hereby incorporated by reference in their entirety.

FIELD OF THE INVENTION

The present invention relates to bioresorbable polymer microparticles derived from structural units comprising caprolactone, polyols and diisocyanates, the manufacture thereof and their use to deliver pharmaceutically active agents.

BACKGROUND OF THE INVENTION

Polycaprolactone (PCL) is among the most common and well-studied bioresorbable polymers. The repeating molecular structure of PCL homopolymer consists of five non-polar methylene groups and a single relatively polar ester group. This high molecular weight polyester is conventionally produced by the ring-opening polymerisation of the cyclic monomer, i.e. ε-caprolactone. A catalyst is used to start the polymerisation and an initiator, such as an alcohol, can be used to control the reaction rate and to adjust the average molecular weight. PCL is a semi-crystalline (~40-50%), strong, ductile and hydrophobic polymer with excellent mechanical characteristics having a low melting point of 60° C. and a glass transition temperature of −60° C.

Poly(ethylene glycol) (PEG) is a biocompatible and highly water soluble (hydrophilic) polymer. Poly(ethylene glycols) are poly(ethylene oxides) containing the repeat unit —$CH_2CH_2O$—. PEG is a highly crystalline (~90-95%) polymer having a low melting point of 60° C. and a glass transition temperature of −55 to −70° C. These difunctional compounds contain hydroxyl end-groups, which can be further reacted and chain extended with diisocyanates or used as initiators for ring-opening polymerisations. PEGs are well-known structural units incorporated into cross-linked polyurethane hydrogels (EP publications EP0016652 and EP0016654) and linear polyurethane hydrogels (PCT publication WO2004029125).

Amphiphilic block copolymers, e.g. PEG-PCL copolymers, have recently attracted attention in the field of medicine and biology as micellar carriers, polymer vesicles and polymer matrices. The triblock copolymer PCL-PEG-PCL has unique phase behaviour in blends and the ability to form polymeric micelle-like core-shell nanostructures in a selective solvent, in which only one block is soluble (*J. Polym. Sci. Part A Polym. Chem.*, 1997, 35, 709-714; *Adv. Drug Delivery Rev.*, 2001, 53, 95-108).

However, the above-mentioned polymers suffer from a number of practical disadvantages. The degradation rate and mechanism appear to depend on a number of factors, such as the chemical structure of the polymer and on the surrounding environmental conditions, such as the degradation media. Two stages have been identified in the degradation process of aliphatic polyesters. Initially, the degradation proceeds by random hydrolytic chain scission of the ester bonds, leading to a decrease in the molecular weight; in the second stage measurable weight loss in addition to chain scission is observed. Another observation is that polycaprolactone degrades much slower than e.g. polylactide. The long degradation time of polycaprolactone (~24 months) is usually a disadvantage for medical applications.

Patent publication WO2005/068533 discloses biodegradable polyurethane polymers formed of prepolymers of caprolactone and polyethylene glycol, reacted with a diisocyanate. The polymers may be used as a drug delivery vehicle, for example as microspheres. However, this publication does not specifically disclose polymers, where the first prepolymer includes a high molecular weight PEG and the second prepolymer includes a low molecular weight PEG.

Our prior patent publication WO2008/047100 describes bioresorbable caprolactone-polyurethane polymers derived from structural units based on caprolactone, poly(alkylene oxide) and diisocyanate for the sustained delivery of active agents. It is an object of the present invention to provide polymers of this general type in microparticle form suitable for administration to patients.

SUMMARY OF THE INVENTION

The present invention provides polymer microparticles, the polymer being a polyurethane derived from structural units comprising poly(alkylene oxide) moieties, caprolactone moieties and urethane moieties; wherein the microparticles have a particle size of from 0.01 to 100 microns.

The microparticles will generally include a pharmaceutically active agent, particularly intended for sustained release.

The invention also relates to the production of the microparticles and to their use to deliver active agent to a patient.

The particle size will vary depending on the target and mode of administration. For example, microparticles intended for administration by injection may generally have a particle size in the range 10 to 100 microns, particularly 15 to 80 microns, especially 20 to 60 microns and advantageously 25 to 50 microns. Microparticles intended for administration as an aerosol may have a particle size in the range 1 to 3 microns apparent aerodynamic diameter. Microparticles intended for intraocular administration into the eye may have a particle size of 0.02 to 2 microns, particularly 0.05 to 1 microns and especially 0.1 to 0.5 microns. Preferably the dispersivity span, which is a measure of the degree of variation in the particle sizes is in the range 1-3, preferably 1.1-2.5, and especially 1.2-2.0.

The particle size may also determine the release profile of the active agent, including the rate of delivery of active agent and the overall time of administration. Release of active agent may be due to diffusion of the active from within the structure of the microparticle. Release may also be due to degradation of the polymer, for example by reduction in molecular weight of the polymer by hydrolysis of ester bonds in the caprolactone moiety leading to escape of the active agent. Release may also be due to loss of mass of the polymer by physical erosion, leading to the liberation of active agent. This erosion mechanism may be particularly relevant to the release of high molecular weight active agents. In any given situation the release mechanism will be a complex interaction of all these, so that the prediction of suitable particle size for a chosen release profile is difficult.

Ultimately, the polymer will be bioresorbed and eliminated from the patient's body.

Thus, the active agent release profile may also be influenced by the reduction in molecular weight of the polymer due to degradation of the polymer, usually by hydrolysis. For example, preferred polymers have a degradation measured by incubation in phosphate buffered saline (PBS) as follows:
1 month at 50° C. mw. reduction of 60 to 90%, particularly 70 to 85%; and
6 months at 37° C. mw. reduction of 30 to 80%, particularly 40 to 70%

The release of active agent is also influenced by the degree of swelling (or the rate of swelling) of the polymer. A high degree of swelling may lead to a faster rate of release of active agent. Preferred swellability in PBS at 37° C. is 0.5 to 1000%, 1-500%, 5-250%, 10-100% and especially 20-70%. For particular uses, the swellability may be chosen in the ranges: 10-30%, 30-60%, 60-100%, 100-150% and 150-225%. High swelling to facilitate rapid polymer breakdown and consequently rapid drug release may be particularly required for pulmonary delivery.

The rate of release will be determined by the active agent and the chosen dose regime. The overall time to release active agent will depend on the therapeutic application and may be of the order of hours, days, weeks, months or even years. Preferred release times are nominally 2 hrs, 24 hrs, 10 days, 30 days, 60 days, 90 days and 120 days. All of the active agent may be released from the microparticle or more likely a large proportion will be released, for example 60%, 70%, 80%, 90% or 95% by weight of the original drug-loading. Initial burst delivery of active agent is generally to be avoided, except for special applications. Generally, a substantially constant release of drug over the effective treatment period is to be preferred.

According to a preferred embodiment of the present invention, the polymer is obtainable by reacting together:
(a) a prepolymer comprising co-polymerised units of a caprolactone and poly(alkylene oxide) moieties;
(b) a polycaprolactone diol comprising co-polymerised units of a caprolactone and a $C_2$-$C_6$ diol; and
(c) a diisocyanate.

Alternatively stated, the invention provides a polymer comprising moieties derived from the stated components (a), (b) and (c) bonded together.

Preferably, the poly(alkylene oxide) moieties of the prepolymer (component (a)), are selected from a poly($C_2$-$C_3$ alkylene oxide) or mixtures thereof. Most preferred is a poly($C_2$ alkylene oxide), e.g. derived from a poly($C_2$ alkylene oxide)diol, i.e. poly(ethylene oxide)diols, for example poly(ethylene glycols). Generally and desirably, the poly (alkylene oxide) moieties should be water soluble to assist in the degradation of the subject polymers in aqueous environments.

Poly(ethylene glycols), which are an example of a polyethylene oxide, may be prepared by the addition of ethylene oxide to ethylene glycol to produce a difunctional polyethylene glycol having the structure $HO(CH_2CH_2O)_nH$ wherein n is an integer from 1 to 800 depending on the molecular weight. Polyethylene oxides contain the repeat unit $(CH_2CH_2O)$ and are conveniently prepared by the stepwise addition of ethylene oxide to a compound containing a reactive hydrogen atom.

The poly(ethylene glycols) used in the present invention are generally linear polyols having an average molecular weight of about 200 g/mol to about 35,000 g/mol, particularly about 300 g/mol to about 10,000 g/mol, especially about 400 g/mol to about 8000 g/mol, for example about 400, 600, 2000, 4000 or 8000 g/mol.

Preferably, therefore, component (a) comprises a co-polymer of caprolactone and a relatively low to middle range molecular weight poly(ethylene glycol).

Component (a) may be made, for example by polymerising together the caprolactone and the polyol comprising poly(alkylene oxide) moieties, to provide a linear dihydroxyl-terminated caprolactone-poly(alkylene oxide) co-polymer for use as a prepolymer in the preparation of the subject polymer.

For example, ε-caprolactone may be reacted, in a ring opening reaction, with a poly(ethylene glycol) to provide a linear dihydroxyl-terminated caprolactone-poly(ethylene glycol) co-polymer for use as a prepolymer in the preparation of the subject polymer.

Such prepolymer typically has an ABA structure e.g. $(CAP)_n$-PEG-$(CAP)_n$, i.e. one having blocks of continuous caprolactone units flanking a PEG unit, e.g. -CAP-CAP-CAP-PEG-CAP-CAP-CAP-, and the average number of continuous units (i.e. the value of n) of caprolactone in each block of the polycaprolactone segments is generally between about 3 to 50, preferably between about 4 to 35, and typically between about 5 to 31, for example, chosen from 5, 9.5 and 31 units.

Typically, in the preparation of component (a), the polymerisation proceeds with the aid of a catalyst. A typical catalyst useful in the polymerisation is stannous octoate, aluminium isopropoxide and/or titanium n-butoxide.

The skilled person will appreciate that in the preparation of the prepolymer (component (a)), the poly(alkylene oxide) moiety, which as mentioned herein above is preferably a poly(ethylene glycol) (i.e. PEG), may be considered as an initiator. The precise reaction conditions used will be readily determined by those skilled in the art. Other co-monomers, co-polymers, and catalysts in this ring-opening polymerisation may be used, if different properties are desired in the product, such as elasticity, degradation and release rate, and the choice of such other ingredients will be apparent to those of skill in the art.

Generally, in the preparation of the prepolymer, the molar ratio of caprolactone to initiator (e.g. the PEG) is generally in the range from 5:1 up to 100:1, for example 10:1 to 50:1, particularly 20:1 to 30:1.

The $C_2$-$C_6$ diol component of the polycaprolactone diol (component (b)), may be any organic diol having a relatively lower molecular weight compared to the poly(alkylene oxide) moiety contained in the prepolymer diol component (a).

For example, the $C_2$-$C_6$ diol, may be chosen from diols having a structure: HO—$(CH_2)_m$—OH, wherein m is a number chosen from 2-6, for example, 1,2-ethylene glycol, 1,4-butane diol, 1,5-pentane diol or 1,6-hexane diol.

Alternatively, the $C_2$-$C_6$ diol may be chosen from diols which are low molecular weight polymers or oligomers chosen from poly(alkylene oxide)diols.

Preferably, such poly(alkylene oxide)diol is selected from a poly($C_2$-$C_3$ alkylene oxide)diol or mixtures thereof. Most preferred are low molecular weight poly($C_2$ alkylene oxide) diols, i.e. low molecular weight poly(ethylene oxide)diols, for example low molecular weight poly(ethylene glycols).

Typically, the low molecular weight poly(ethylene glycol) has the following structure: HO—$(CH_2CH_2O)_n$—H, wherein n is a number chosen from 2 or 3, i.e. low molecular weight polyethylene glycols are preferred. An alternatively preferred diol is ethylene glycol itself (i.e. wherein n is 1).

The most preferred diol is diethylene glycol, i.e. an ethylene glycol dimer, which has the structure HO—$CH_2CH_2$—O—$CH_2CH_2$—OH.

Generally and desirably, the $C_2$-$C_6$ diol should be water soluble to assist in the degradation of the subject polymers in aqueous environments.

The caprolactone moiety of the polycaprolactone diol (component (b)) is preferably derived from ε-caprolactone. Thus, the polycaprolactone diol is preferably derived from ε-caprolactone in a ring opening reaction using the low molecular weight diol as an initiator which itself becomes incorporated into the polycaprolactone diol. For example, such polycaprolactone diol, may be prepared by reacting ε-caprolactone and diethylene glycol in a ring opening reaction to provide a linear dihydroxyl-terminated poly(co-caprolactone-diethylene glycol). A catalyst may be used in the preparation of the polycaprolactone diol. Suitable catalysts include stannous octoate, aluminium isopropoxide and/or titanium n-butoxide.

The ratio of caprolactone to low molecular weight diol initiator may be chosen according to principles readily available to the skilled person. Typically, when low molecular weight poly(ethylene glycol) is used as the low molecular weight diol, the ratio of caprolactone:ethylene glycol is of the order of about 4: about 2, and the co-polymer may have the following structure as an example: OH-CAP-CAP-EG-EG-CAP-CAP-OH, where CAP represents the opened caprolactone ring in the appropriate orientation, i.e. the unit —$(CH_2)_5C(O)O$— or —$O(O)C(CH_2)_5$— and EG represents an ethylene glycol unit. It will be appreciated that the order and positioning of the CAP units in the co-polymer molecules may vary.

The diisocyanate component (c) is preferably 1,4-butane diisocyanate, 1,6-hexamethylene diioscyanate, or L-lysine diisocyanate etc.

Such diisocyanates are particularly suitable for applications in which toxic degradation products are to be avoided, e.g. in biomedical applications.

1,4-butane diisocyanate is preferred.

Known biomedical and biodegradable polyurethanes usually contain aromatic, cycloaliphatic or aliphatic diisocyanates, which may produce toxic substances or fragments upon degradation. It is generally accepted that, in the degradation of polyurethanes, any unreacted diisocyanate structural units hydrolyze to their corresponding amines. Most of these diamines are known to be toxic, carcinogenic and/or mutagenic. In the international publication WO9964491, the use of the non-toxic 1,4-butane diisocyanate (BDI) is shown in the manufacture of biomedical polyurethanes having a uniform block-length. The Applicant of the present invention considers that the use of 1,4-butane diisocyanate has a number of advantages because on degradation it yields 1,4-butane diamine, also known as putrescine, which is present in mammalian cells. (*J. Polym. Bull.*, 1997, 38, 211-218).

Thus, an additional advantage of at least one embodiment of the present invention is the use of biocompatible starting materials in the manufacture of the polyurethanes, which produce non-toxic, biocompatible polymers and degradation products.

However, in applications in which the toxicity of the degradation products is not as important, any diisocyanate commonly used to form polyurethanes may be used, (including those listed above) and including diisocyanates such as, dicyclohexylmethane-4,4-diisocyanate and diphenylmethane-4,4-diisocyanate.

The bioresorbable polymers of the present invention may degrade in the physiological environment of animals and the degradation products are eliminated through the kidneys or completely bioabsorbed. According to one definition, biodegradable polymers require enzymes or micro-organisms for hydrolytic or oxidative degradation. But in general, a polymer that loses its mass over time in the living body is called an absorbable, resorbable, bioresorbable or biodegradable polymer. This terminology is applied in the present invention regardless of polymer degradation mode, in other words for both enzymatic and non-enzymatic degradation and/or erosion.

The polymers of the present invention degrade in water, aqueous buffer solutions, physiological fluids, soil, compost, sea water and fresh water, and the like over extended time periods. The composition of the polymer and the temperature may cause different degradation rates, which may be readily determined by the skilled person. Sometimes, the active agent will have been mostly delivered before significant mass loss (e.g. less than 5 wt %, less than 2 wt % or less than 1 wt %) has occurred. In other cases, especially the delivery of proteins, mass-loss may contribute significantly to delivery of active agent.

Generally, in use, the polymer may be subjected to a temperature of from 10° C. to 95° C., preferably from 25° C. to 45° C., typically from 30° C. to 38° C., e.g. 37° C.

The time taken for the polymer to fully degrade, i.e. lose all of its mass, may vary widely, e.g. typically of the order of from one day to 250 weeks, preferably one week to 150 weeks, preferably from 2 weeks to 100 weeks, e.g. from 2 weeks to 60 weeks, such as 4 weeks or 52 weeks.

The degradation time can be tailored for the intended final application.

As indicated above, the polymerisation process used to manufacture the bioresorbable polymer of the present invention typically involves a ring-opening polymerisation and a polyaddition reaction to obtain high molecular weight poly (block-caprolactone-co-PEG) urethanes. Accordingly, the present invention also extends to the process used to manufacture the polymers.

The polymer may be prepared by:
(1) providing:
   (a) a prepolymer comprising co-polymerised units of a caprolactone and poly(alkylene oxide) moieties;
   (b) a polycaprolactone diol comprising co-polymerised units of a caprolactone and a $C_2$-$C_6$ diol; and
   (c) a diisocyanate; and
(2) reacting components (a), (b) and (c) together.

In the preparation of the subject polymer, the prepolymer component (a) can be reacted with components (b) and (c) to provide the final polymer. Preferably, the prepolymer is first combined, such as by admixing (for example by blending) with component (b), followed by reaction with component (c) diisocyanate.

The skilled person will appreciate that other modes of operation may be used to produce the polymers.

The component (a) prepolymer is generally produced by polymerising together caprolactone and a poly(alkylene oxide)diol. Preferably a catalyst is used during this polymerisation reaction. The reaction is preferably conducted in an inert atmosphere, such as under an atmosphere of dry nitrogen gas.

Suitable catalysts include stannous octoate, aluminium isopropoxide and/or titanium n-butoxide.

By using different molar ratios of component (a) (prepolymer), component (b) (e.g. poly(co-caprolactone-diethylene glycol) and diisocyanate (e.g. BDI), the phase structure, degradation rate and mechanical properties of the end polymer products may be tailored. The skilled person may judiciously choose the ratios of components and the reaction times, temperatures and other conditions appropriate to provide the final desired polymer product properties.

Generally, the mole ratio of component (a) to component (b) to component (c) is in the range of 0.02-2.0 to 1.0 to 1.02-3.0, particularly 0.15-1.5 to 1.0 to 1.2-2.5, particularly 0.2-1.0 to 1.0 to 1.25-2.0. A preferred range is 0.25-1.0 to 1.0 to 1.25-2.0.

As described herein above, the present invention typically employs a two-step polymerisation method, which includes a ring-opening polymerisation and chain extending reaction, in the manufacture of the subject bioresorbable polymer. This straightforward two-step process offers a number of versatile possibilities for tailoring the structure and properties of the polymer components (a) and (b), and the final polymer, thus enabling the polymer to be used for a wide variety of purposes. Numerous monomers and low molecular weight polymers may be introduced during the described steps of the synthesis, either during manufacture of components (a) or (b), or during preparation of the final polymer. Thus, a wide variety of polymer properties may be obtained in the final polymer using the above-mentioned materials by changing the molar composition. The present invention provides a solution to the typical drawbacks encountered with caprolactone/PEG-based copolymers, which include limited structure-property variations, slow degradation and dissolution rates.

Generally, any conventional polymerisation reactor may be used in the manufacture of the polyurethanes presented in the current invention, e.g. batch reactor, continuous stirred tank reactor (CSTR), extruder, reactive injection moulding (RIM), tube reactor, pipe reactor and/or melt mixer. Further processing of these biodegradable polymers can be done by using conventional processing methods suitable for thermoplastic polymers e.g. injection moulding, extrusion, pultrusion, blow moulding, vacuum moulding, solvent casting and other moulding and casting techniques, as well as dispersion, foam and film forming techniques.

Only a few monomers and polymers appear to fulfil the required demands for tailored, non-toxic bioresorable polymers. Copolymerisation may be used to increase the degradation rate, and the degradation rate of caprolactone copolymers may be altered by varying the structure of the comonomers, the molar composition and the polymer molecular weight. The degradation media may also affect the degradation behaviour.

The polymer microparticles of the present invention may usefully be applied as drug delivery devices. The phase behaviour of the polymers consisting of a highly crystalline block and a rubbery block combined with the very hydrophilic and hydrophobic nature of each block makes them desirable as drug delivery systems because the permeability of each individual component or phase for different loaded drugs can differ widely depending on the properties of the particular drug loaded in the polymer. Furthermore, the flexible processes of the invention allow the properties of the polymer to be selected to suit a desired drug, and tailor how the drug is loaded and then released from the polymer. This offers the opportunity to generate a desired release profile for a chosen drug.

The bioresorbable polymer microparticles of the present invention may be applied to a wide range of uses, and such uses are included within the scope of the present invention. The polymer microparticles may be used as a matrix for drug delivery systems. Potentially any drug could be loaded into the bioresorbable polymer microparticles of the present invention. The microparticles can be used as separate isolated particles or in forms where the microparticles are fused into a solid matrix.

The present invention, therefore, also provides controlled release compositions comprising the bioresorbable polymer microparticles containing an active agent. The active agent may be a pharmaceutically active agent for human or animal use. A particular feature of the controlled release composition is that fast drug release can be achieved without any lactide or glycolide content.

The polymer microparticles of the present invention may be prepared using any of the techniques readily available to the skilled person. In particular, microparticles have been successfully prepared by precipitating microparticles using double emulsion techniques. In a water-in-oil-in-water (W/O/W) emulsion technique, the active agent is dissolved in water to produce a solution and this solution is emulsified in an organic solvent containing the dissolved polymer (the "oil") to produce a water-in-oil emulsion. This emulsion is then homogenised into water to form the final water-in-oil-in-water emulsion. The solvent is then removed e.g. by evaporation, to precipitate the microparticles.

In the solid-in-oil-in-water (S/O/W) technique, the active agent in solid form is emulsified in the oil (rather than the active agent solution as in the W/O/W (technique). The solid active agent may be used alone. In the case of proteins and peptides, the active agent may be recrystallised by itself or with a co-crystalline material (e.g. an amino acid) to form mono-crystals or co-crystals. The solid active agent may be used in the form of protein-coated microcrystals. The particle size of the crystals may be in the region 1-50 microns, especially 2-25 microns.

The microparticles may be prepared in the presence or absence of added surfactant, for example Tween. The use of surfactant tends to favour larger microparticle size.

Pharmaceutically active agents of particular interest include:

Proteins such as interferon alpha, beta and gamma, insulin, human growth hormone, leuprolide; peptides such as oxytocin antagonists; enzymes and enzyme inhibitors; Benzodiazepines (e.g. midazolam); Anti-migraine agents (e.g. triptophans, ergotamine and its derivatives); Anti-infective agents (e.g. azoles, and treatments for bacterial vaginosis or candida); and opthalmic agents (e.g. latanoprost).

A detailed list of active agent includes $H_2$ receptor antagonist, antimuscarinics, prostaglandin analogue, proton pump inhibitor, aminosalycilate, corticosteroid, chelating agent, cardiac glycoside, phosphodiesterase inhibitor, thiazide, diuretic, carbonic anhydrase inhibitor, antihypertensive, anti-cancer, anti-depressant, calcium channel blocker, analgesic, opioid antagonist, antiplatelet, anticoagulant, fibrinolytic, statin, adrenoceptor agonist, beta blocker, antihistamine, respiratory stimulant, micolytic, expectorant, benzodiazepine, barbiturate, anxiolytic, antipsychotic, tricyclic antidepressant, $5HT_1$ antagonist, opiate, $5HT_1$ agonist, antiemetic, antiepileptic, dopaminergic, antibiotic, antifungal, anthelmintic, antiviral, antiprotozoal, antidiabetic, insulin, thyrotoxin, female sex hormone, male sex hormone, antioestrogen, hypothalamic, pituitary hormone, posterior pituitary hormone antagonist, antidiuretic hormone antagonist, bisphosphonate, dopamine receptor stimulant, androgen, non-steroidal anti-inflammatory, immuno suppressant local anaesthetic, sedative, antipsioriatic, silver salt, topical antibacterial, vaccine.

DETAILED DESCRIPTION

Embodiments of the present invention will be described by way of example only.

Synthesis of the polyurethanes is a two-step polymerisation reaction. The first step is ring opening of caprolactone using PEG and stannous octoate as a catalyst, yielding a PCL-PEG-PCL block copolymer, referred to as the pre-polymer. The pre-polymer is then chain extended with polycaprolactone-diol and butane diisocyanate to form the final biodegradable polyurethane. Polycaprolactone-diol is the reaction product of caprolactone and diethylene glycol. The final polymers can be referred to as segmented polyurethanes, as they are believed to undergo microphase separation into hard blocks and soft blocks. In very general terms, the soft block is composed of the pre-polymer and the hard block is composed of the polycaprolactone-diol and urethane moiety (derived from the diisocyanate).

We incorporate bioactive molecules into microspheres made from the biodegradable polyurethane in order to produce a vehicle which allows for controlled release of the bioactive compound from the biodegradable polymer matrix. The aim of this experimental work was to synthesise microparticles using bovine serum albumin (BSA) as a representative protein molecule in either a solid or aqueous form using emulsion solvent evaporation technology. During this process, bioactive molecules can be entrapped in polymer microspheres, which can then be collected. In a water-in-oil-in-water (w/o/w) emulsion, bioactive molecules in the aqueous form are homogenised with polymer dissolved in an organic solvent to form a water-in-oil emulsion. This w/o emulsion is then transferred to a second aqueous phase and homogenised again to form a final w/o/w emulsion.

Bioactive molecules can also be added directly into the polymer phase in a solid form, forming a final solid-in-oil-in-water (s/o/w) emulsion. The bioactive in solid form is homogenised with polymer dissolved in an organic solvent forming a solid-in-oil emulsion. This s/o emulsion is then transferred to an aqueous phase and homogenised to form the final s/o/w emulsion. We tested the particle size and distribution of microparticles containing BSA formed using BSA in the aqueous or the solid form, as recrystallised mono-crystals or co-crystals. The experiments were performed both with and without the presence of surfactants (Tween 80, PEG6000, PVP and PVA,). PVP is polyvinylpyrrolidone; PVA is polyvinyl acetate.

Example 1: Manufacture of Linear Bioresorbable Prepolymers with Different Structure and Block Lengths for Subsequent Polyurethane Synthesis The length of PEG block (400, 2000 and 8000 g/mol) and caprolactone block (500-3500 g/mol) was changed. The target pre-polymer molecular weight was selected to be between 7000-11 000 g/mol. Pre-polymer batch sizes were about 500-600 g. The pre-polymers were prepared by varying their compositions as follows (see Table 1): Batch A) Prepolymer A made of 32.01 g PEG 400 (16.0 mol-%), 561.58 g caprolactone (98.4 mol-%) and 0.608 g tin(II) octoate (0.03% mol-%), targeting a theoretical molecular weight of 7418 g/mol, Batch B) Prepolymer B made of 149.81 g PEG2000 (2.0 mol-%), 418.84 g caprolactone (97.9 mol-%) and 0.45 g tin(II)octoate (0.03 mol-%), targeting a theoretical molecular weight of 7592 g/mol, Batch C) Prepolymer C made of 461.93 g PEG8000 (10.0 mol-%). 59.30 g caprolactone (90.0 mol-%) and 0.07 g tin(II)octoate (0.03 mol-%), targeting a theoretical molecular weight of 9027 g/mol. Batch D) Prepolymer D made of 394.86 g PEG2000 (2.0 mol-%). 1103.95 g caprolactone (97.97 mol-%) and 1.20 g tin(II) octoate (0.03 mol-%), targeting a theoretical molecular weight of 7592 g/mol.

TABLE 1

Synthesised prepolymers for the present invention

| Prepolymer Name | PEG | Theoretical MW of prepolymer | Theoretical MW of PCAP block | Number of CL units in PCAP black | Reaction Temperature (° C.), time |
|---|---|---|---|---|---|
| Prepolymer A | 400 | 7418 | 3509 | 31 | 155, 5 h |
| Prepolymer B | 2000 | 7592 | 2796 | 24.5 | 155, 6 h |
| Prepolymer C | 8000 | 9027 | 514 | 4.5 | 155, 5 h |
| Prepolymer D | 2000 | 7592 | 2796 | 24.5 | 155, 5 h |

The molecular weights (Mn and Mw) and molecular weight distributions were measured for various prepolymers by a triple angle light scattering combined with size exclusion chromatography (SEC) system, see Table 2.

TABLE 2

Prepolymers were characterised using SEC coupled with light scattering.

| Prepolymer Name | Mn (g/mol) SEC | MWD SEC |
|---|---|---|
| Prepolymer A | 10,711 | 1.34 |
| Prepolymer B | 9,072 | 1.27 |
| Prepolymer C | 10,525 | 1.00 |
| Prepolymer D | 13,731 | 1.43 |

Example 2: Manufacture of a Linear Bioresorbable Hydrogel Prepolymer and Polymer (Prepolymer A and Polymer 1)

Into a stirred tank reactor 32.01 g (16.0 mol-%) of dried PEG400 (MW 400 g/mol), 561.58 g caprolactone (98.4 mol-%) and 0.608 g (0.03 mol-%) tin(II) octoate were fed in that order. Dry nitrogen was continuously purged into the reactor. The reactor was pre-heated to 155° C. using an oil bath and a mixing speed of 60 rpm. PEG400 was dried and melted in a rota-evaporator prior to being added into the reactor. Then, ε-caprolactone was added and finally the catalyst tin(II) octoate. Prepolymerisation time for the PEG-PCL prepolymer was 5 hours. The theoretical molecular weight of the prepolymer was 7418 g/mol.

For the polymer preparation 6.60 g of low molecular weight poly(ε-caprolactone)diol (MW 530 g/mol) (PCLDI) and 90.2 g of the above mentioned prepolymer were dried and melted in a rota-evaporator prior to being added into the reactor. Dry nitrogen was continuously purged into the reactor. The reactor was pre-heated to 110° C. using an oil bath and a mixing speed of 75 rpm. 2.21 ml of 1,4-butane diisocyanate (BDI), at a molar ratio of 1:1:2 PEG-PCL prepolymer: PCLDI: BDI, were fed into the reactor. Polymerisation time was 6 minutes. Polymer was scraped into an aluminium pan and stored in a desiccator for further testing. (Polymer 1)

DSC analysis revealed that the glass transition temperature ($T_g$) and the melting point ($T_m$) were −57.1 and 52.2° C. respectively.

Example 3: Manufacture of a Linear Bioresorbable Polymer with a Different Structure Prepolymer B (Table 1 in Example 1), and polycaprolactone diol (MW ~530 g/mol) were mixed, dried and melted under vacuum at 90° C. for at least one hour prior to feeding them into the preheated (110° C.) reactor. Reaction mixture was mixed (75 rpm) under nitrogen. 1,4-butane diisocyanate was fed into the reactor. The molar ration between prepolymer, poly(ε-caprolactone)diol and BDI was 1:1:2. The reaction times was 13 minutes.

DSC analysis revealed that there were two glass transition temperatures ($T_g$) at −53.7 and 1.6° C. and the melting point ($T_m$) was 51.3° C.

Example 4: Manufacture of a Linear Bioresorbable Polymer with a Different Structure The chain extending polymerisation was performed as in Example 3, except the prepolymer was Prepolymer C in Table 1 in Example 1. The reaction time was 15 minutes.

DSC analysis revealed that the glass transition temperature ($T_g$) and the melting point ($T_m$) were −59.1 and 53° C. respectively.

Example 5: Manufacture of a Linear Bioresorbable Polymer with a Different Structure The chain extending polymerisation was performed as in Example 3, except the prepolymer was Prepolymer C in Table 1 in Example 1 and the molar ratio between prepolymer, poly(ε-caprolactone)diol and BDI was 0.25:1.75:2. The reaction time was 12 minutes.

DSC analysis revealed that the glass transition temperature ($T_g$) was −38.6° C. and there were two melting endotherms ($T_m$) at 51.1 and 95.9° C.

Example 6: Manufacture of a Linear Bioresorbable Polymer with a Different Structure The chain extending polymerisation was performed as in Example 3, except the prepolymer was Prepolymer C in Table 1 in Example 1 and the molar ration between prepolymer, poly(ε-caprolactone)diol and BDI was 0.05:1.95:2. The reaction time was 20 minutes.

Example 7: Manufacture of a Linear Bioresorbable Polymer with a Different Structure The chain extending polymerisation was performed as in Example 3, except the prepolymer was Prepolymer D in Table 1 in Example 2. The reaction time was 20 minutes.

DSC analysis revealed that the polymer had a glass transition temperatures ($T_g$) of −62.5 and 10.6° C. and the melting point ($T_m$) was 52.3° C.

TABLE 3

Synthesised bioresorbable polymers for the present invention.

| Polymer Name | PEG | Prepolymer Name | Theoretical MW of prepolymer | Theoretical MW of CAP block | Prepolymer | CAP-diol Mol | BDI Ratio | Reaction Temperature (° C.), time |
|---|---|---|---|---|---|---|---|---|
| Polymer 1 | 400 | Prepolymer A | 7418 | 3509 | 1 | 1 | 2 | 110, 6 min |
| Polymer 2 | 2000 | Prepolymer B | 7592 | 2796 | 1 | 1 | 2 | 110, 13 min |
| Polymer 3 | 8000 | Prepolymer C | 9027 | 514 | 1 | 1 | 2 | 110, 15 min |
| Polymer 4 | 8000 | Prepolymer C | 9027 | 514 | 0.25 | 1.75 | 2 | 110, 12 min |
| Polymer 5 | 8000 | Prepolymer C | 9027 | 514 | 0.05 | 1.95 | 2 | 110, 20 min |
| Polymer 6 | 2000 | Prepolymer D | 7592 | 2796 | 1 | 1 | 2 | 110, 20 min |

Example 8

Molecular weight determination was carried out for a selected number of bioresorbable polymers, which are shown in Table 4. The molecular weight of the polymer will determine its mechanical properties and have an impact on its degradation properties; therefore the importance of determining molecular weight values is evident.

These types of polymers are expected to have a molecular weight of 100,000 ($M_n$) in the best of cases. The minimum value for the $M_n$ to have reasonable mechanical properties or to consider the compound a polymer is 30,000. In the present invention molecular weight values of $M_n$ exceeded our expectations and values of around 80,000 were obtained in most cases.

TABLE 4

Molecular weight analyses for selected bioresorbable polymers.

| Example Number | Polymer Name | PEG | Prepolymer Name | Mw (g/mol) SEC | Mn (g/mol) SEC | MWD SEC |
|---|---|---|---|---|---|---|
| 2 | Polymer 1 | 400 | Prepolymer A | 158,124 | 88,428 | 1.79 |
| 3 | Polymer 2 | 2000 | Prepolymer B | 132,328 | 77,345 | 1.71 |

TABLE 4-continued

Molecular weight analyses for selected bioresorbable polymers.

| Example Number | Polymer Name | PEG | Prepolymer Name | Mw (g/mol) SEC | Mn (g/mol) SEC | MWD SEC |
|---|---|---|---|---|---|---|
| 4 | Polymer 3 | 8000 | Prepolymer C | 100,009 | 83,869 | 1.19 |
| 5 | Polymer 4 | 8000 | Prepolymer C | 116,019 | 94,375 | 1.24 |
| 6 | Polymer 6 | 2000 | Prepolymer D | 80,992 | 56,215 | 1.45 |

Example 9: Processing of Thermoplastic Polymers by Using a Hot-Press—Film Production Bioresorbable Polymers 1, 2, 3, 4 and 6 from Table 3 were dried under vacuum over night prior to processing them using the hot-press. Upper and lower plate temperatures were set at 160° C. Two Teflon sheets were placed between the mould and the hot plates. The melting time was 2 min followed by a 30 second holding under pressure (~170 bar). An exact amount of polymer was used to fill the mould. After cooling to room temperature samples were mechanically punched out and kept in the freezer for further analysis.

Example 10: Polymer Degradation and Swelling Investigation at 37° C. and 50° C. in Phosphate Buffered Saline Solution In order to prove the bioresorbability of synthesised polymers and their potential to release bioactive agents, a number of polymers were selected to carry out biodegradation and swelling studies.

Polymer samples for degradation studies and swelling were made from the biodegradable polymers by hot-pressing films and punching specimens out of it. There were two different types of degradation studies: one at 37° C. in phosphate buffered saline solution pH 7.4 for twelve months and an accelerated study at 50° C. in phosphate buffered saline solution pH7.4 for twelve months where applicable. At the beginning samples were taken every week and after one month once a month or even less frequently.

The degradation and swelling results at for Polymer 1 can be seen in Table 5.

TABLE 5

Swelling and erosion of Polymer 1 incubated in PBS buffer at 37° C. and 50° C.

| Incubation time | Average swelling (%) | | Average mass remaining (%) | |
|---|---|---|---|---|
| | 37° C. | 50° C. | 37° C. | 50° C. |
| One day | 1 | 2 | 99 | 99 |
| One week | 0 | 1 | 99 | 99 |
| One month | 1 | 0 | 99 | 99 |
| Two months | −1 | 1 | 97 | 99 |
| Three months | 0 | 1 | 98 | 98 |
| Six months | 1 | 0 | 99 | 98 |
| Twelve months | — | — | 98 | 87 |

The degradation and swelling results at for Polymer 2 can be seen in Table 6.

TABLE 6

Swelling and erosion of Polymer 2 incubated in PBS buffer at 37° C. and 50° C.

| Incubation time | Average swelling (%) | | Average mass remaining (%) | |
|---|---|---|---|---|
| | 37° C. | 50° C. | 37° C. | 50° C. |
| One day | 17 | 30 | 98 | 99 |
| One week | 18 | 31 | 99 | 99 |
| One month | 19 | 21 | 99 | 99 |
| Two months | 17 | 29 | 99 | 99 |
| Three months | 17 | 31 | 99 | 97 |
| Six months | 20 | 30 | 99 | 96 |
| Twelve months | ND | ND | 98 | 91 |

The degradation and swelling results for Polymer 3 can be seen in Table 7. The dissolution of this polymer in PBS was rapid and therefore swelling measurements were only possible in the first 5 minutes of the study.

TABLE 7

Swelling and erosion of Polymer3 incubated in PBS buffer at 37° C. and 50° C.

| Incubation time | Average swelling (%) | | Average mass remaining (%) | |
|---|---|---|---|---|
| | 37° C. | 50° C. | 37° C. | 50° C. |
| One minute | 91 | ND | ND | ND |
| Two minute | 108 | ND | ND | ND |
| Three minutes | 107 | ND | ND | ND |
| Four minutes | 164 | ND | ND | ND |
| Five minutes | 212 | ND | ND | ND |

The degradation and swelling results for Polymer 4 can be seen in Table 8. The dissolution of this polymer in PBS was rapid and therefore swelling and erosion measurements were only possible in the first six hours of the study.

TABLE 8

Swelling and erosion of Polymer 4 incubated in PBS buffer at 37° C. and 50° C.

| Incubation time | Average swelling (%) | | Average mass remaining (%) | |
|---|---|---|---|---|
| | 37° C. | 50° C. | 37° C. | 50° C. |
| One hour | 150 | 143 | 91 | 91 |
| Two hours | 221 | 231 | 88 | 88 |
| Three hours | 254 | 234 | 84 | 91 |
| Four hours | 237 | 244 | 83 | 79 |
| Six hours | 282 | 244 | 81 | 63 |

The degradation and swelling results at for Polymer b can be seen in Table 9.

TABLE 9

Swelling and erosion of Polymer 6 incubated in PBS buffer at 37° C. and 50° C.

| Incubation time | Average swelling (%) | | Average mass remaining (%) | |
|---|---|---|---|---|
| | 37° C. | 50° C. | 37° C. | 50° C. |
| One day | 18 | 33 | 98 | 99 |
| One week | 18 | 33 | 99 | 99 |
| One month | 18 | 38 | 99 | 99 |

TABLE 9-continued

Swelling and erosion of Polymer 6 incubated
in PBS buffer at 37° C. and 50° C.

| Incubation time | Average swelling (%) | | Average mass remaining (%) | |
| --- | --- | --- | --- | --- |
| | 37° C. | 50° C. | 37° C. | 50° C. |
| Two months | 19 | 43 | 99 | 99 |
| Three months | 19 | 45 | 99 | 97 |
| Six months | ND | ND | 99 | 96 |

Example 11: Preparation of Microparticles Using a 5% Polymer in Dichloromethane (DCM) Solution with Tween 80® as a Surfactant 0.5 g of Polymer 6 was dissolved in 10 g DCM, forming an oil phase (O). 0.1 g of bovine serum albumin (BSA) was dissolved in 0.5 g of distilled water (dH$_2$O) forming the inner aqueous phase (W$_1$). 1.5 g Tween 80® was dissolved in 48.5 g of dH$_2$O to form the outer aqueous phase (W$_2$). W$_1$ and O were homogenised at 4000 rpm for 5.5 min, using a high shear mixer to form a water-in-oil (W$_1$/O) emulsion. 5 g of the resulting W$_1$/O emulsion was transferred to the outer aqueous phase (W$_2$) and homogenised at 7000 rpm to form the final water-in-oil-in-water (W$_1$/O/W$_2$) emulsion. The emulsion was stirred at 650 rpm for 24 hours, using a magnetic stirrer, in order to remove the solvent from the oil phase.

Example 12: Preparation of Microparticles Using a 5% Polymer in DCM Solution without Surfactant The formulation was prepared as in Example 11, except that the outer aqueous phase consisted of 50 g of dH$_2$O only.

Example 13: Preparation of Microparticles Using a Solid Protein Formulation, a 5% Polymer in DCM Solution with Tween 80® as a Surfactant The formulation was prepared as in Example 11, except that BSA was used in a solid formulation (as a co-crystal with valine) as opposed to an aqueous phase. 0.1 g of this solid BSA formulation was added directly to the oil phase and homogenised, forming a solid-in-oil (s/o) emulsion.

Example 14: Preparation of Microparticles Using a Solid Protein Formulation, a 5% Polymer in DCM Solution without a Surfactant The formulation was prepared as in Example 11, except that BSA was used in a solid formulation (as a co-crystal with valine) as opposed to an aqueous phase. 0.1 g of this solid BSA formulation was added directly to the oil phase and homogenised, forming a solid-in-oil (s/o) emulsion. The outer aqueous phase consisted solely of 50 g of dH$_2$O.

Example 15: Preparation of Microparticles Using a 2.5% Polymer in DCM Solution with Tween 80® as a Surfactant The formulation was prepared as in example 11, except that 0.25 g of polymer was dissolved in 10 g DCM in order to form a 2.5% polymer solution.

Example 16: Preparation of Microparticles Using a 5% Polymer in DCM Solution with Tween 80® as a Surfactant The formulation was prepared as in example 11 except the rate of addition of the (W$_1$/O) emulsion to W$_2$ was decreased.

Example 17: Preparation of Microparticles Using a 1% Polymer in Ethyl Acetate (EA) Solution with Tween 80® as a Surfactant The formulation was prepared as in Example 11, except that 0.1 g of polymer was dissolved in 10 g EA.

Example 18: Preparation of Microparticles Using a 2.5% Polymer in EA Solution with Tween 80® as a Surfactant The formulation was prepared as in Example 11, except that 0.25 g of polymer was dissolved in 10 g EA.

Example 19: Preparation of Microparticles Using a 5% Polymer in EA Solution with Tween 80® as a Surfactant The formulation was prepared as in Example 11, except that 0.5 g of polymer was dissolved in 10 g EA.

Example 20: Preparation of Microparticles Using a 1% Polymer in EA Solution with PEG6000 as a Surfactant The formulation was prepared as in Example 11, except that 0.1 g of polymer was added to 10 g EA and the outer aqueous phase consisted of 1.5 g of PEG6000 in 48.5 g dH$_2$O.

Example 21: Preparation of Microparticles Using a 1% Polymer in EA Solution with PVP as a Surfactant The formulation was prepared as in Example 11, except that 0.1 g of polymer was added to 10 g EA and the outer aqueous phase consisted of 1.5 g of PVP in 48.5 g dH$_2$O.

Example 22: Preparation of Microparticles Using a 1% Polymer in EA Solution with PVA as a Surfactant The formulation was prepared as in Example 11, except that 0.1 g of polymer was added to 10 g EA and the outer aqueous phase consisted of 1.5 g of PVA in 48.5 g dH$_2$O.

Example 23: Particle Size Determination of Microparticles

Dynamic light scattering is a method that can be used to determine the particle size distribution of the microparticles formed. In dynamic light scattering particle sizing the volume median diameter D(v,0.5) is the diameter where 50% of the particle size distribution is above and 50% is below. The D(v,0.9), is the value where 90% of the volume distribution is below this value. The D(v,0.1), is the value where 10% of the volume distribution is below this value. The span is the width of the distribution based on the 10%, 50% and 90% quantile as shown in the equation below:

$$\text{Span} = \frac{D[v, 0.9] - D[v, 0.1]}{D[v, 0.5]}$$

Figure 1:
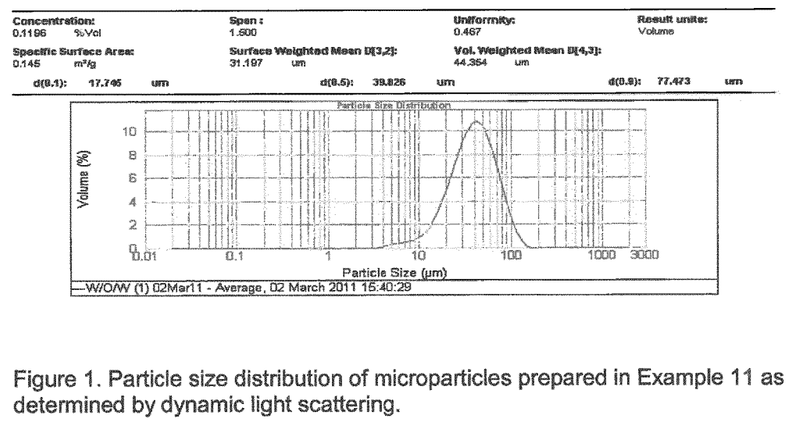
FIG. 1 shows particle size distribution of microparticles prepared in Example 11 as determined by dynamic light scattering.

Various microparticle preparations were collected after solvent removal and centrifugation and added directly to dH$_2$O (acting as the dispersing medium) in the Malvern Mastersizer, stirring at 2000 rpm and sized. FIG. 1 shows a typical size distribution curve obtained from Microparticles prepared in Example 11.

Table 10 summarises the average particle size (D(v, 0.5) and the size distribution (Span) for microparticles prepared in Example 11, Example 12, Example 13, Example 14, Example 15, Example 16, Example 18, Example 19, Example 20, Example 21, Example 22.

TABLE 10

The D(v, 0.5) and Span for various microparticles preparations prepared in Example 11 to Example 22.

| Microparticles | Batch no. | |
|---|---|---|
| | D(v, 0.5) | Span |
| Example 11 | 39.8 | 1.5 |
| Example 12 | 68.9 | 1.3 |
| Example 13 | 26.8 | 2.3 |
| Example 14 | 117.3 | 3.5 |
| Example 15 | 98.3 | 6.8 |
| Example 16 | 71.2 | 1.8 |
| Example 18 | 23.2 | 7.1 |
| Example 19 | 50.8 | 2.7 |
| Example 20 | 1621.5 | 1.3 |
| Example 21 | 31.2 | 8.2 |
| Example 22 | 23.9 | 8.0 |

Example 24: Image Analysis of Microparticles

Figure 2:
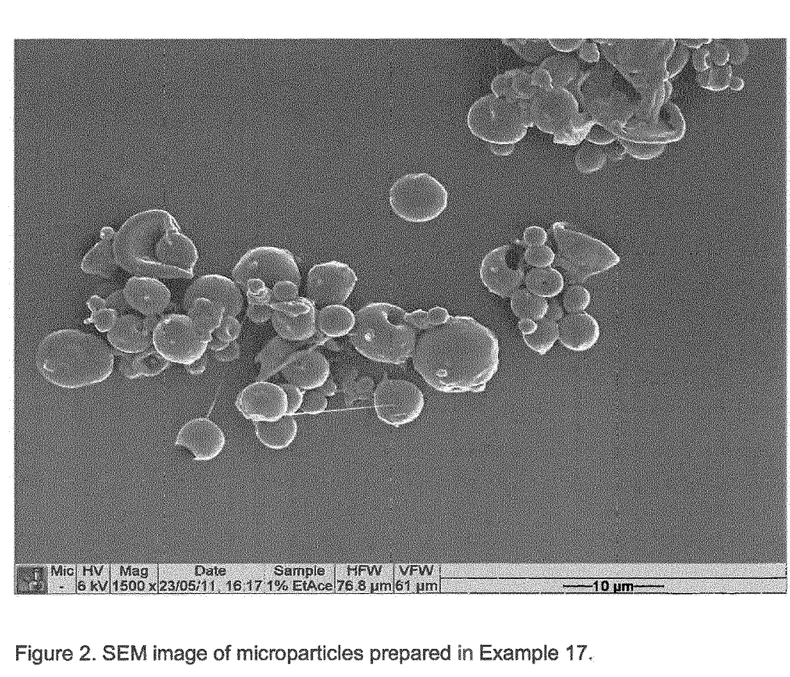
FIG. 2 shows an SEM image of microparticles prepared in Example 17.

Scanning Electron Microscopy (SEM) is a technique commonly used to study particle morphology. Microparticles prepared in Example 17 were gold-coated before imaging using a Polaron SC515 SEM coating system. They were then viewed on a JEOL 6400 scanning electron microscope. Images were captured using Scandium software. FIG. 2 shows the formation of generally spherical particles with an average particle size less than 10 microns in size.

The invention claimed is:

1. Polymer microparticles, the polymer being a polyurethane obtainable by reacting together:
   (a) a prepolymer comprising co-polymerised units of a caprolactone and poly(alkylene oxide) moieties;
   (b) a polycaprolactone diol comprising co-polymerised units of a caprolactone and a C$_2$-C$_6$ diol; and
   (c) a diisocyanate;
   wherein the microparticles have a particle size of from 0.01 to 100 microns, and
   wherein the microparticles have a dispersivity span in the range from 1 to 3;
   wherein the dispersivity span is the width of particle size distribution as defined by the formula:

$$\text{Span} = \frac{D[v, 0.9] - D[v, 0.1]}{D[v, 0.5]}$$

wherein:
D(v, 0.5) is the median volume diameter wherein 50% of the particle size distribution has a volume-based diameter above the D(v,0.5) value and 50% is below;
D(v, 0.9) is the value wherein 90% of the particle size distribution has a volume-based diameter below the D(v, 0.9) value; and
D(v, 0.1) is the value wherein 10% of the particle size distribution has a volume-based diameter below the D(v,0.1) value.

2. The microparticles to claim 1, which further comprise an active agent.

3. The microparticles to claim 2, wherein the active agent is a protein or peptide.

4. The microparticles of claim 1, in a formulation suitable for injection, having a particle size of 15 to 80 microns.

5. The microparticles of claim 1, in an aerosolizable formulation that upon aerosolization provides an aerosol having an apparent aerodynamic diameter in the range 1 to 3 microns.

6. The microparticles of claim 1, in a formulation suitable for intraocular use, having a particle size of 0.02 to 2 microns.

7. The microparticles of claim 1, wherein after 1 month at 50° C. in phosphate buffered saline the reduction in average molecular weight of the polymer is 60 to 90%.

8. The microparticles of claim 1, wherein after 6 months at 37° C. in phosphate buffered saline the reduction in average molecular weight of the polymer is 30 to 80%.

9. The microparticles of claim 1, wherein the swellability in phosphate buffered saline at 37° C. is 10-100%.

10. The microparticles of claim 2, wherein the active agent is released by 30 days nominally.

11. The microparticles of claim 1, which become completely resorbed in the body of a human or animal patient.

12. A method for delivering an active agent to a patient comprising administering microparticles according to claim 2 to the patient.

13. The microparticles of claim 8, wherein after 6 months at 37° C. in phosphate buffered saline the reduction in average molecular weight of the polymer is 40 to 70%.

14. The microparticles of claim 1, wherein the dispersivity span is in the range 1.1-2.5.

15. The microparticles of claim 1, wherein the dispersivity span is in the range 1.2-2.0.

16. The microparticles of claim 7, wherein after 1 month at 50° C. in phosphate buffered saline the reduction in average molecular weight of the polymer is 70 to 85%.

17. The microparticles of claim 2, wherein the active agent is released by 60 days nominally.

18. The microparticles of claim 2, wherein the active agent is released by 90 days nominally.

19. The microparticles of claim 2, wherein the active agent is released by 120 days nominally.

20. The microparticles of claim 1, wherein the microparticles degrade in the physiological environment of animals.

21. The microparticles of claim 20, wherein the time taken for the polymer to fully degrade is in the order of from 1 day to 250 weeks.

22. The microparticles of claim 1, wherein the swellability in phosphate buffered saline at 37° C. is in the range from 1 to 500%.

23. The microparticles of claim 2, wherein the overall time to release the active agent is in the order of hours.

24. The microparticles of claim 2, wherein the overall time to release the active agent is in the order of days.

25. The microparticles of claim 2, wherein the overall time to release the active agent is in the order of weeks.

26. The microparticles of claim 2, wherein the overall time to release the active agent is in the order of months.

27. The microparticles of claim 2, wherein the overall time to release the active agent is in the order of years.

28. The microparticles of claim 1, wherein the poly(alkylene oxide) moieties are selected from a poly($C_2$-alkylene oxide), a poly($C_3$-alkylene oxide), and mixtures thereof.

29. The microparticles to claim 1, wherein the $C_2$-$C_6$ diol is selected from ethylene glycol and diethylene glycol.

\* \* \* \* \*